US00PP25127P3

(12) United States Plant Patent
Skelton

(10) Patent No.: US PP25,127 P3
(45) Date of Patent: Dec. 2, 2014

(54) KIWIFRUIT PLANT NAMED 'Y356'

(50) Latin Name: *Actinidia chinensis*
Varietal Denomination: Y356

(71) Applicants: Frederick James Lewis, Gisborne (NZ); Simon Charles Dickie, Gisborne (NZ)

(72) Inventor: Donald Alfred Skelton, Rangiriri (NZ)

(73) Assignees: Simon Charles Dickie, Gisborne (NZ); Frederick James Lewis, Gisborne (NZ)

( * ) Notice: Subject to any disclaimer, the term of this patent is extended or adjusted under 35 U.S.C. 154(b) by 15 days.

(21) Appl. No.: 13/986,324

(22) Filed: Apr. 22, 2013

(65) Prior Publication Data

US 2014/0317792 P1 Oct. 23, 2014

(51) Int. Cl.
*A01H 5/08* (2006.01)

(52) U.S. Cl.
USPC ..... Plt./156

(58) Field of Classification Search
CPC ..... A01H 5/08
USPC ..... Plt./156
See application file for complete search history.

*Primary Examiner* — June Hwu
*Assistant Examiner* — Keith Robinson

(57) ABSTRACT

A kiwifruit plant particularly distinguished by very early maturing fruit, hairless fruit surface with conspicuous mid brown lenticels, yellow fruit flesh, ovoid longitudinal and circular cross section fruit shape, slightly blunt protruding stylar end, is described.

7 Drawing Sheets

Genus and species: *Actinidia chinensis*.
Variety denomination: 'Y356'.

BACKGROUND OF THE INVENTION

The present invention relates to a new and distinct variety of *Actinidia chinensis* (kiwifruit) hereinafter referred to by the cultivar name 'Y356' or the 'new plant'. 'Y356' was selected from a population of seedlings derived from crossing two kiwifruit selections 'R5' (unpatented), the female, and 'RY' (unpatented), the non-fruiting male, using controlled pollination in the course of a planned kiwifruit variety breeding program. The cross was made in October 2004 by Donald Alfred Skelton at Rangiriri, New Zealand.

The new plant has been asexually propagated in Rangiriri, New Zealand by grafting and the unique combination of characteristics of the new plant has been found to be reproducible and stable in successive generations of propagation. In order to obtain true-to-type clones of the initial plant, asexually propagated plants were obtained by grafting dormant buds from the original seedling onto rootstock.

Plant Variety rights application for 'Y356' was filed in New Zealand on 20 Jul. 2007 and assigned the application number KIW030. Plant Breeders rights for 'Y356' was filed in Australia on 15 Feb. 2010 and assigned the application number 201/029. Propagation material of 'Y356' has never been sold or made publically available prior to the filing of this application.

SUMMARY OF THE INVENTION

The following are the most outstanding and distinguishing characteristics of the new plant when grown under normal horticultural practices in Te Puke, New Zealand:

1. Very early maturing fruit
2. Hairless fruit surface with conspicuous mid brown lenticels
3. Yellow fruit flesh 4. Ovoid longitudinal and circular cross section fruit shape
5. Slightly blunt protruding stylar end

DESCRIPTION OF THE PHOTOGRAPHS

The new plant is illustrated by the accompanying photographs which show in full color typical specimens of the plant habit, foliage, fruit and flowers of the new variety 'Y356'. The colors shown are as true as can be reasonably obtained by conventional photographic procedures. The photographs include a plant approximately one year old after grafting on *Actinidia deliciosa* 'Bruno' (unpatented) rootstock in optimum conditions in Te Puke, New Zealand.

DESCRIPTION OF THE NEW CULTIVAR

Figure 1:
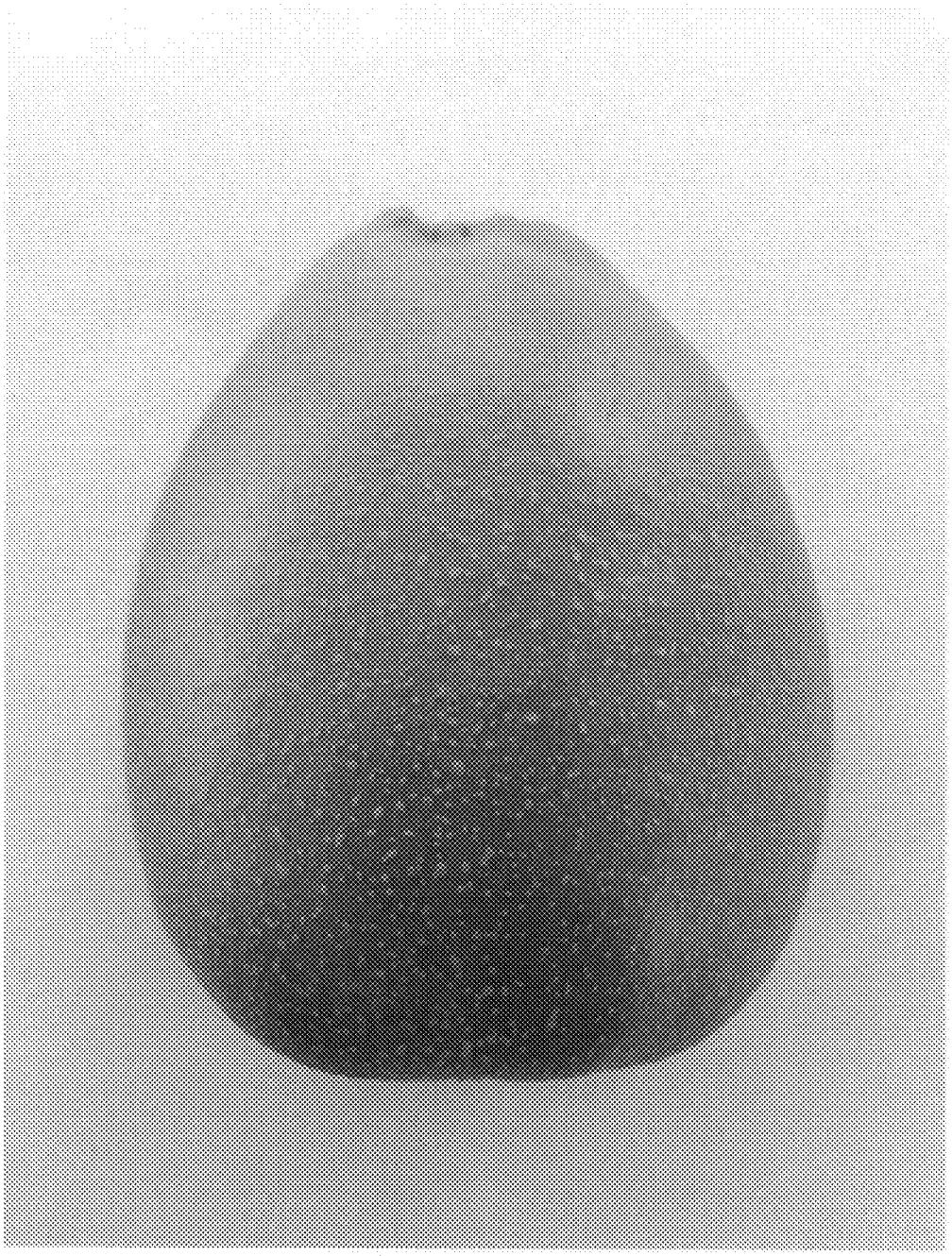
FIG. 1 shows typical ripe whole fruit in the studio
Figure 2:
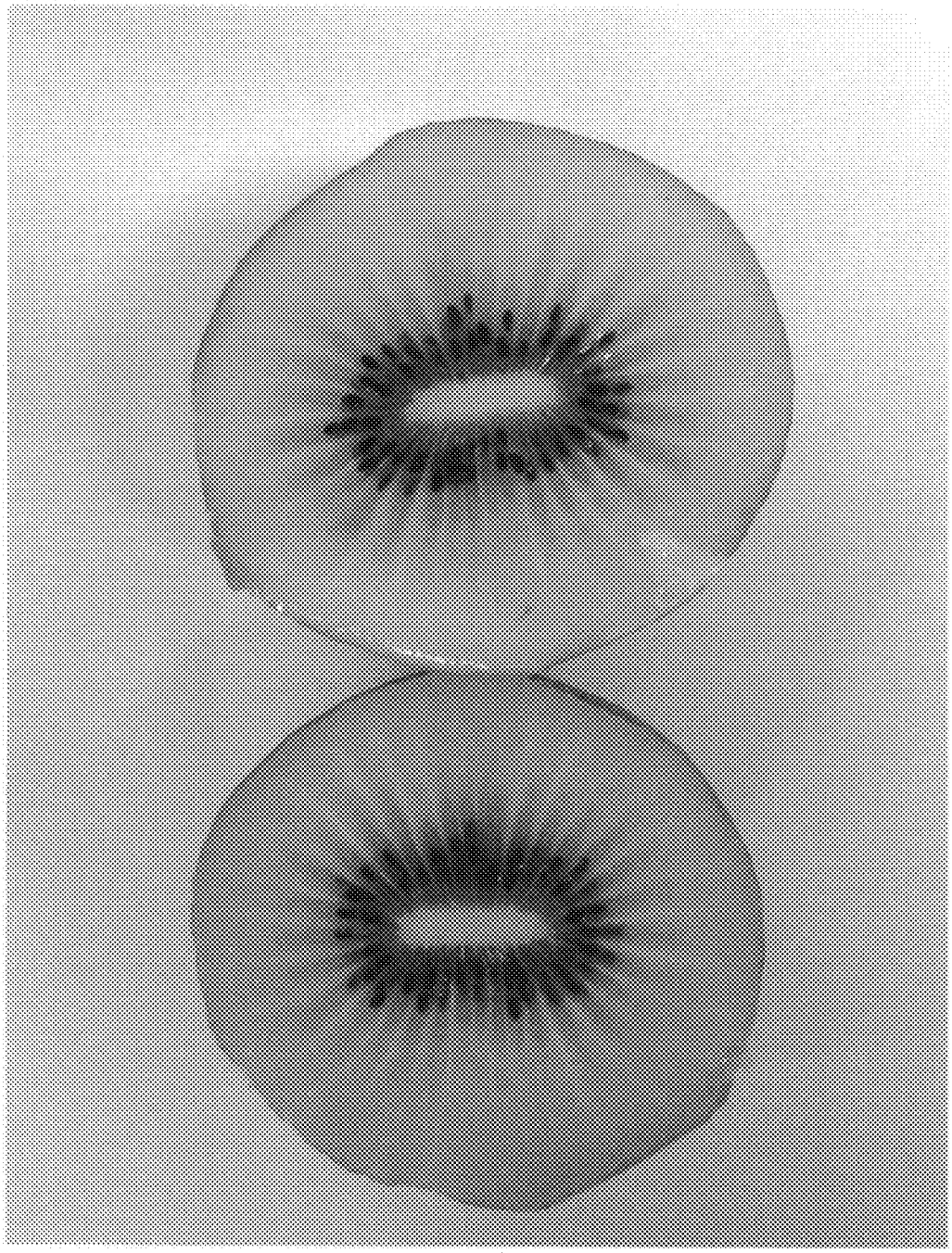
FIG. 2 shows typical fruit cross section in the studio
Figure 3:
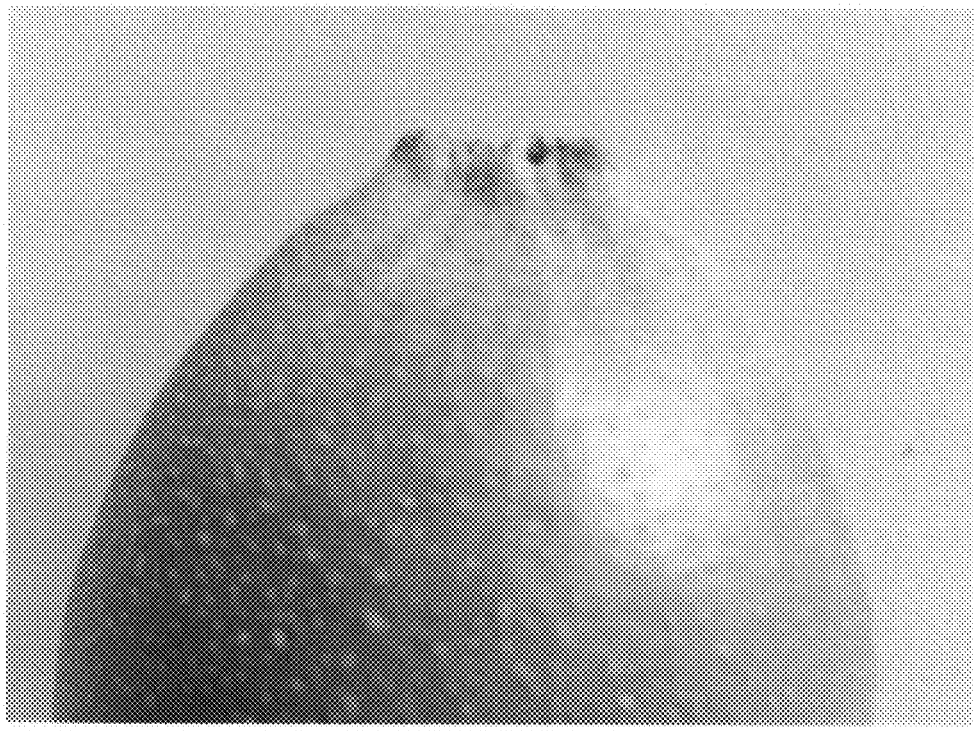
FIG. 3 shows typical whole fruit in the studio—stylar end, side view
Figure 4:
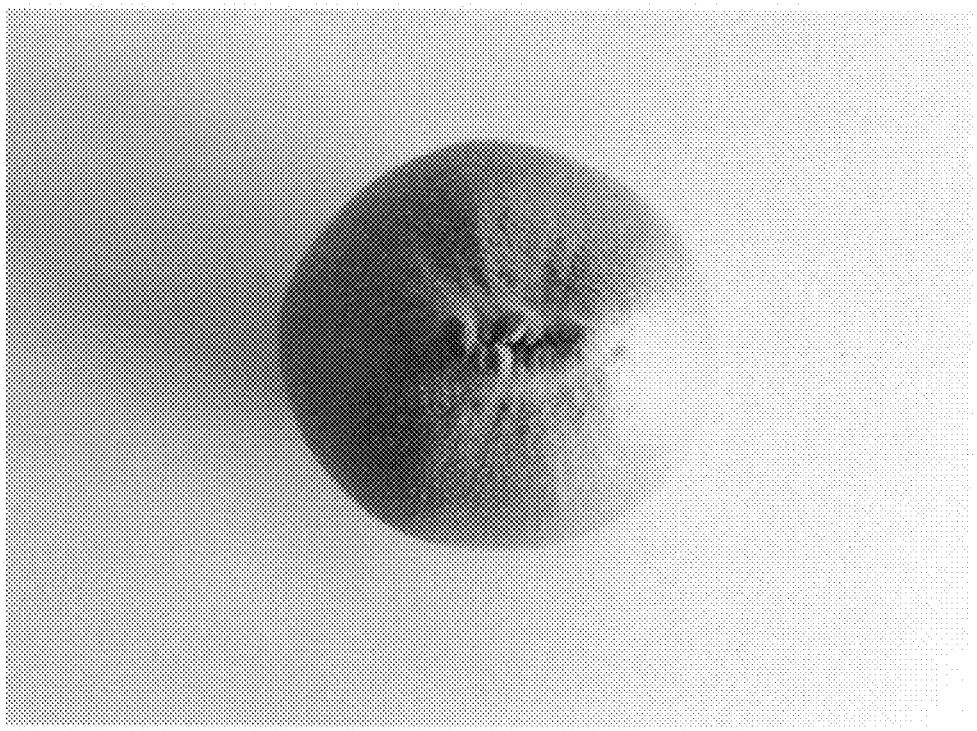
FIG. 4 shows typical whole fruit in the studio—stylar end, top view
Figure 5:
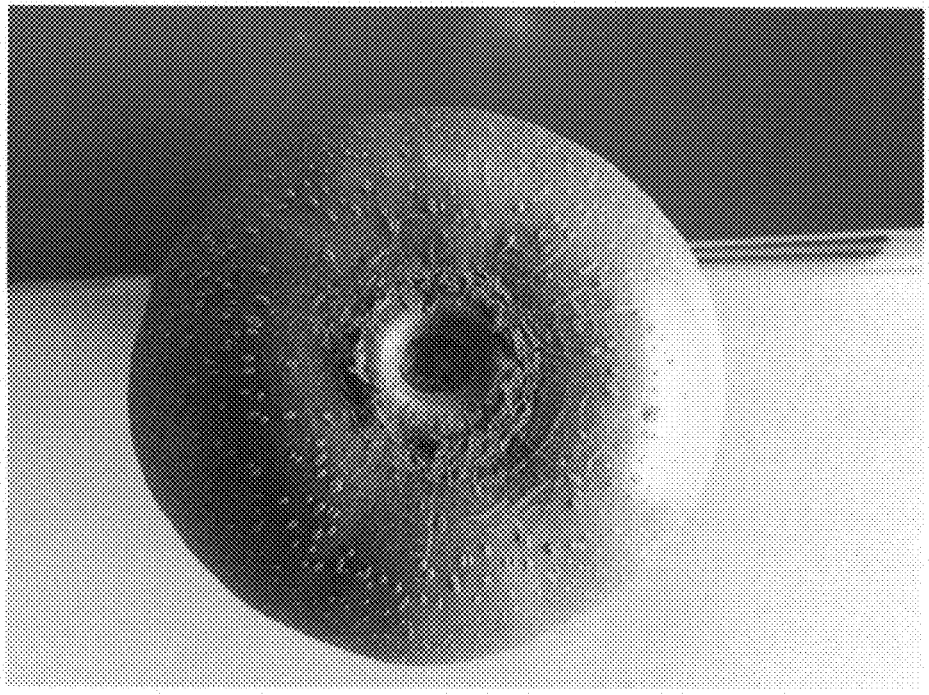
FIG. 5 shows typical whole fruit in the studio—stem end, top view
Figure 6:
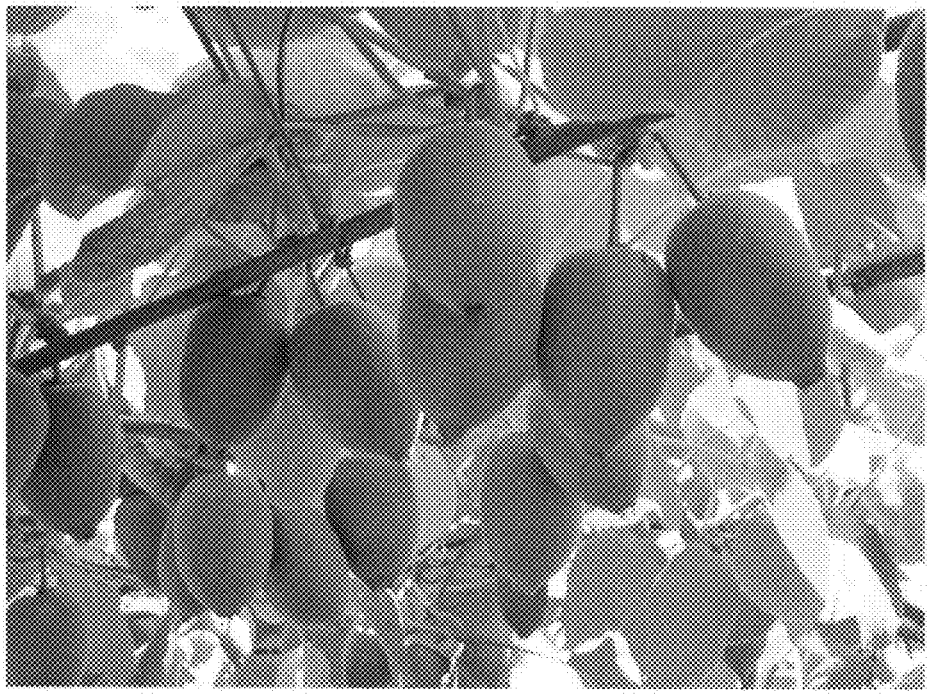
FIG. 6 shows typical fruit on the vine
Figure 7:
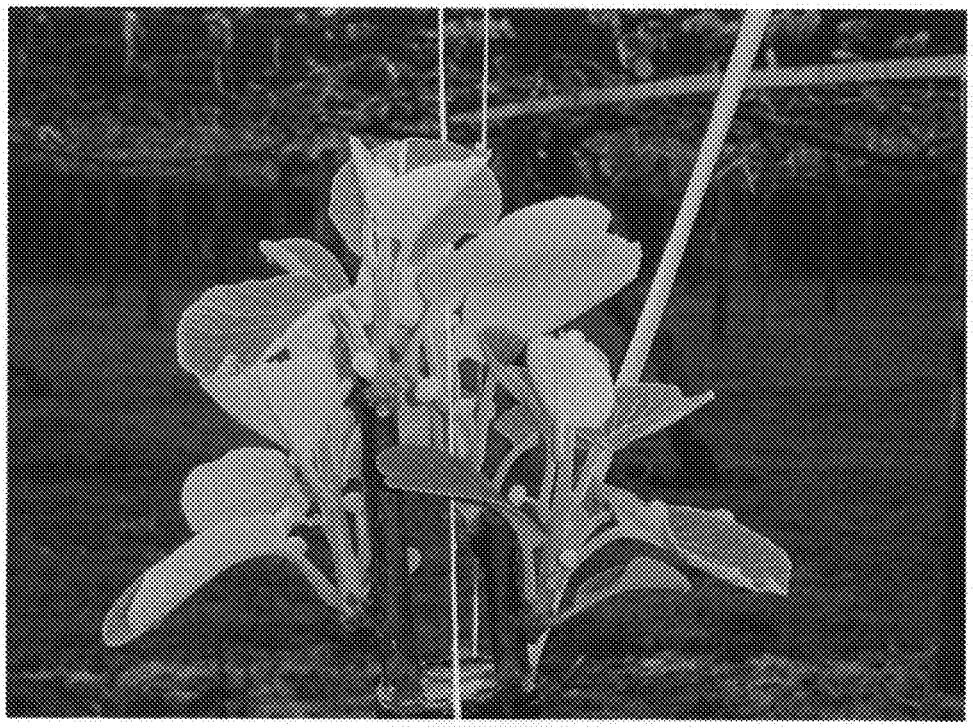
FIG. 7 shows grafted plant with flower buds
Figure 8:
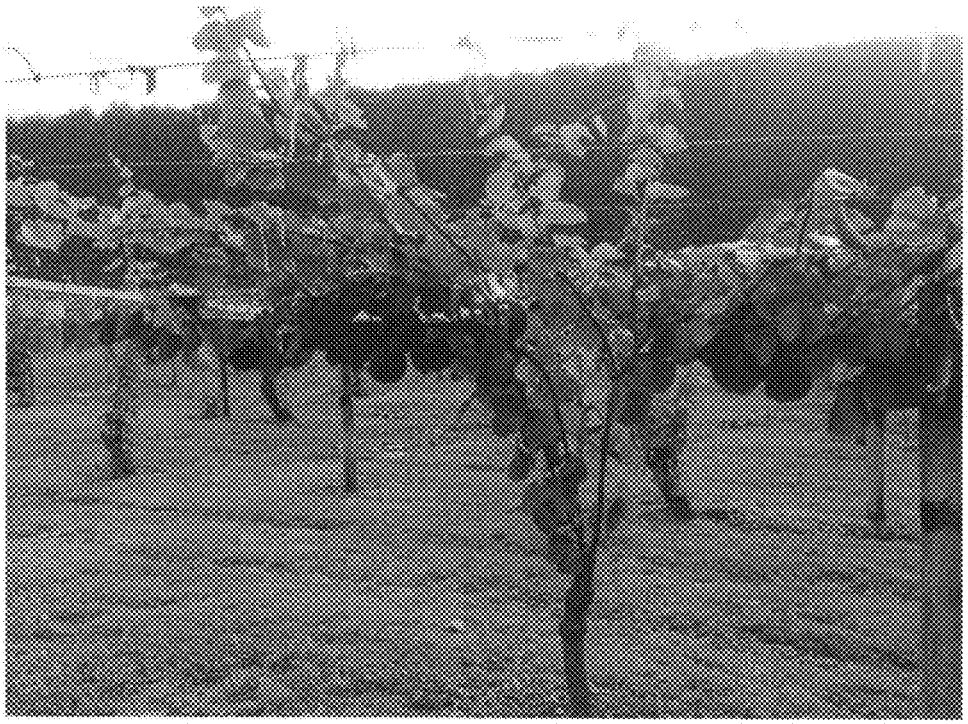
FIG. 8 shows one year old grafted plant
Figure 9:
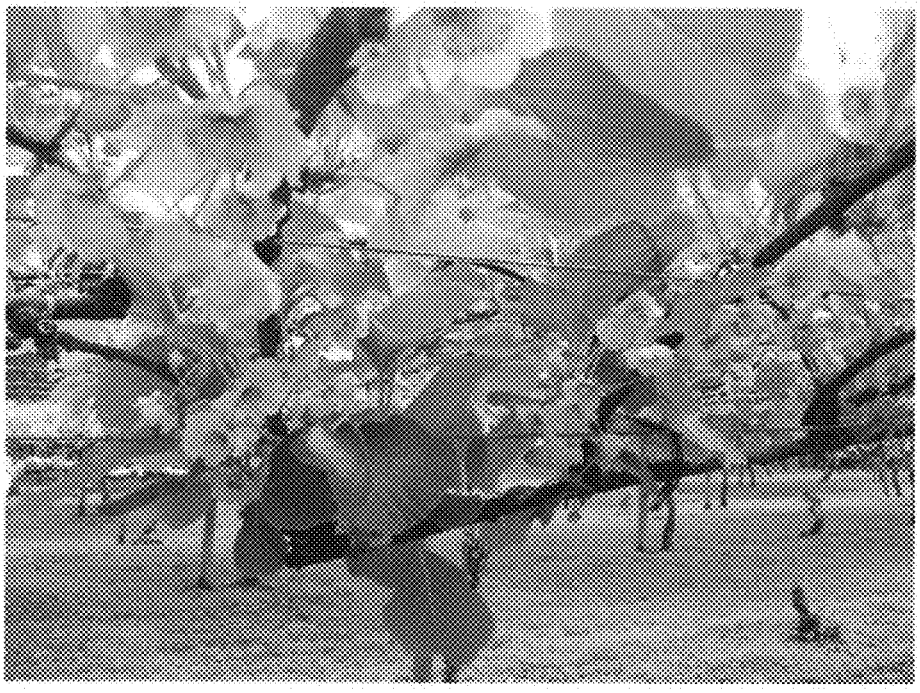
FIG. 9 shows flowers on the vine
Figure 10:
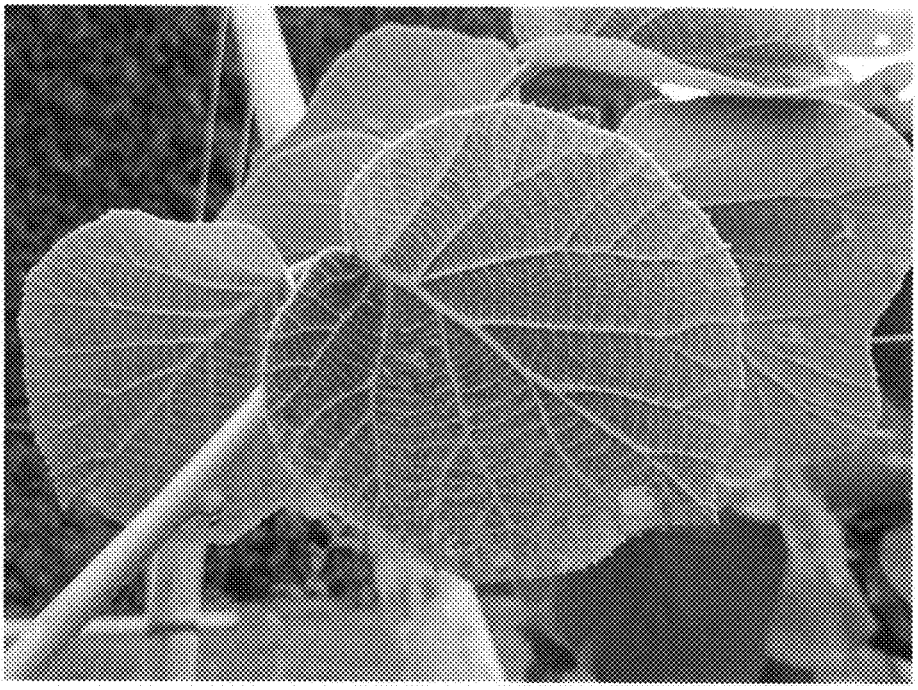
FIG. 10 shows very young leaf on the vine
Figure 11:
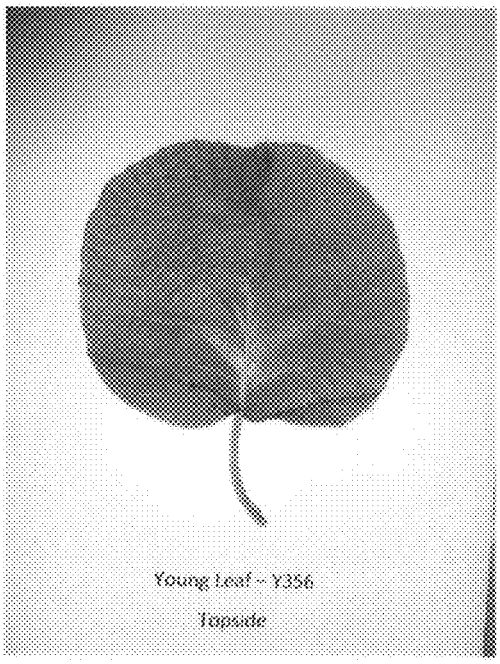
FIG. 11 shows top side of young leaf in the studio from above (adaxial surface).
Figure 12:
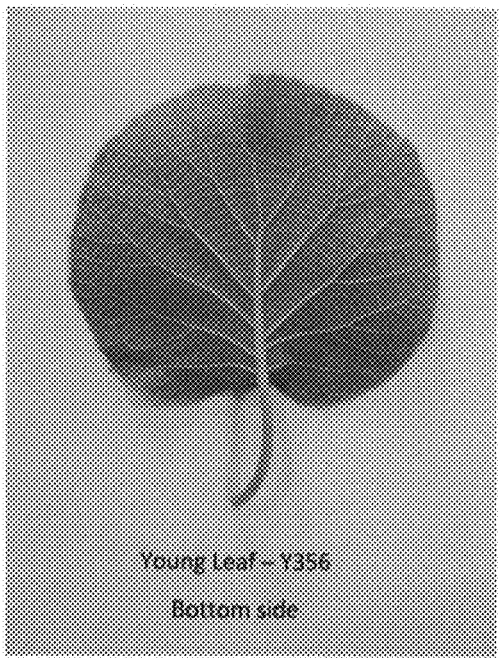
FIG. 12 shows bottom side of young leaf in the studio from below (abaxial surface).
Figure 13:
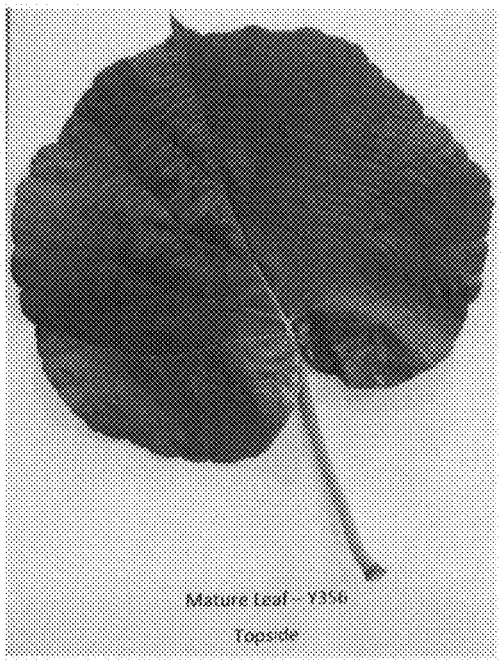
FIG. 13 shows top side of mature leaf in the studio from above (adaxial surface).
Figure 14:
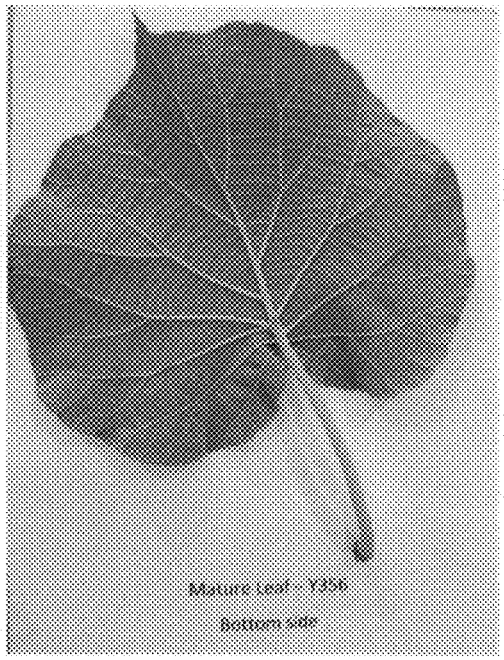
FIG. 14 shows bottom side of mature leaf in the studio from below (abaxial surface).

The following detailed description sets forth the distinctive characteristics of 'Y356'. The following observations, measurements and values were made on three year old vines grafted onto 'Bruno' (unpatented) rootstock, and managed under standard orchard practice. Random measurements of each characteristic were obtained from samples of 6 plants unless otherwise stated.

Horticultural terminology is used in accordance with UPOV guidelines for kiwi. All dimensions are in millimetres, and all weights are in grams (unless otherwise stated). Certain characteristics of this variety, such as growth and color, may change with changing environmental conditions (e.g., light, temperature and moisture), nutrient availability, rootstocks, or other factors. Color readings were taken in natural light. Color references are primarily to the 1995 edition of the Colour Chart published by The Royal Horticultural Society, London (R.H.S.), except where general colours of ordinary significance are used.

DETAILED BOTANICAL DESCRIPTION

Classification:

*Family*.—Actindiaceae.

*Botanical name*.—*Actinidia chinensis*.

*Common name*.—Kiwifruit.

Parentage:

*Female parent*.—A kiwifruit selection 'R5' (unpatented).

*Male parent*.—A kiwifruit selection 'RY' (unpatented).

Plant:

*Plant habit*.—Female plant of twining habit and strong vigour, producing many one year old canes and large leaves.

*Average plant size*.—plants are grown on a standard pergola structure at a height of 1.8 m, each plant was pruned to occupy a canopy area of approximately 15 $m^2$.

*Ploidy*.—Diploid.

*Propagation*.—Grafting of dormant buds onto rootstock and micro propagation by tissue culture.

Shoots:

*Texture of young shoots*.—Minutely, sparsely pubescent with small brown hairs.

*Colour of young shoots*.—Yellow-green, RHS 144B.

*Diameter of mature shoots*.—6.5 mm to 7.5 mm.

*Texture of mature shoots*.—Smooth with weakly conspicuous raised lenticels.

*Colour of mature shoots*.—Greyed-orange, RHS 166B.

*Lenticels on shoots*.—Quantity/density: sparse. Size: 0.5 mm by 1.5 mm. Shape: narrowly elliptical. Colour: greyed-orange, RHS 165C.

Leaves:

*Quantity per one metre of mature shoot*.—16 to 22.

*Arrangement*.—Alternate.

*Length* (*mature leaf*).—130 mm to 170 mm.

*Width* (*mature leaf*).—130 mm to 190 mm.

*Shape*.—Cordate to orbicular.

*Apex*.—Rounded with broad cuspidate tip.

*Base*.—Cordate, some overlapping.

*Margin*.—Ciliate.

*Leaf spines*.—Not present.

*Texture*.—Upper surface: leathery with weak puckering. Lower surface: minutely pubescent, with more dense hairs on main veins.

*Colour*.—Young leaves, upper surface: yellow green, RHS 144A with red anthocyanin colouration RHS 46A on very young immature leaves. Young leaves, lower surface: yellow green, RHS 147C. Mature leaves, upper surface: yellow green, RHS 146A. Mature leaves, lower surface: yellow green, RHS 146D.

*Venation*.—Pattern: reticulate. Colour, upper surface: yellow green, RHS 153A. Colour, lower surface: yellow green, RHS 153D.

*Petiole* (*leaf stem*).—Length: 70 mm to 130 mm. Diameter (cross section) 1 mm to 2 mm. Colour: yellow, RHS 10D with weak red anthocyanin colouration RHS 46A on the upper side on young leaves. Texture: smooth.

Inflorescence:

*Inflorescence type*.—One king flower with occasional 1-2 smaller side flowers.

*Natural flowering season*.—First flowers early October, with a flowering period of approximately 14 days.

*Flower number per square metre*.—50 to 60.

*Fragrance*.—Absent.

*Longevity of viable flowers on the plant*.—4 days.

*Pedicel* (*stalk holding each flower*).—Strength: strong. Length: 35 mm to 40 mm. Colour: yellow green, RHS 145B. Texture: minutely, sparsely pubescent.

*Flowers*.—Flower bud (diameter): 8 mm to 12 mm. Flower bud (length): 7 mm to 11 mm. Colour of bud: greyed green, RHS 191C. Shape of bud: round to slightly flattened. Diameter of individual flower: average 50 mm (king flower). Arrangement of petals: overlapping.

*Petals*.—Quantity: 6 to 10 (average 8). Length: 19 mm to 26 mm. Width: 16 mm to 21 mm. Type of colouration: Colour, primary when fully opened: white, 155D. Colour, base of petals and centre (inside) when fully opened: yellow, 4D.

*Sepals*.—Quantity: >5. Length: 8 mm (average). Width: 4 mm (average). Colour: greyed green, RHS 191D.

Reproductive organs:

*Styles*.—Quantity: 30-32 (average). Attitude: semi erect. Colour: white, RHS 155D.

*Stamens*.—Quantity: 60 to 70.

*Anthers*.—Colour: yellow orange, RHS 17A.

*Ovary*.—(king flower). Length: 10 mm. Shape: Ovoid. Colour: white, RHS 155D.

Fruit:

*Length*.—75 mm (average).

*Diameter*.—53 mm (average).

*Weight range*.—70 g to 210 g.

*Average weight*.—110-115 g.

*Shape*.—Longitudinal: ovoid. Stylar end: weakly protruding. Shoulder: broad. Cross section: circular.

*Stalks*.—Length: 35 mm to 40 mm. Diameter: 3 mm to 4 mm. Texture on mature fruit: smooth, no pubescence. Colour on mature fruit: grey brown, RHS 199A.

*Skin*.—

*Colour* (*at harvest*).—Yellow-green RHS 152B. Texture: Hairless with conspicuous lenticels. Adherence to flesh: moderate.

*Lenticels*.—Quantity: dense. Colour: greyed orange RHS 164A. Size: 1-2 mm (diameter).

*Pericarp*.—Outer colour, early: yellow green RHS 150B. Outer colour, mature: yellow, RHS 11A. Inner colour, mature: yellow green, RHS 11B. Hue angle: Reaches a hue angle of 103° approximately 140 days (varies with season) after full bloom.

*Core of fruit*.—Colour, mature: yellow, RHS 4C. Quantity of locules: average 30. Quantity of Seeds: average 25 per transverse slice through middle of fruit. Colour of seeds: greyed purple, RHS 187A.

*Flavour*.—Taste: sweet tropical flavour. Texture: smooth. Dry matter at harvest: 19-20% average. Brix level at harvest: 8% average. Brix level at consumption: 16-17% average.

Rootstock: Y356 commonly grown on "*Actinidia deliciosa*" 'Bruno' (unpatented) rootstock.

Vegetative bud break:

*Timing*.—Early September.

*Quantity of buds breaking*.—95%.

*Crop load*.—40-50 per square meter average after thinning.

*Leaf senescence*.—Late April, early May.

Disease resistance: No observations made.

Insect resistance: No observations made.

Temperature tolerance: Tolerates low temperatures to approximately −5° C. without negative effects, tolerates high temperatures to approximately 35° C. without negative effects.

COMPARISON WITH PARENTAL AND KNOWN CULTIVARS

When compared to the commercial variety 'Hort16A' (U.S. Plant Pat. No. 11,066); 'Y356' has slightly later flowering, significantly earlier fruit maturation, reaches a hue angle of 103° 10-14 days earlier, a circular fruit cross section and a less protruding stylar end.

When compared to the commercial variety 'Y374' (U.S. Plant Pat. No. 21,174); 'Y356' has a hairless fruit skin, dense conspicuous brown lenticels on the fruit skin and a lighter average fruit weight.

When compared to the female parent 'R5' (unpatented); 'Y356' has a much heavier average fruit weight, fruit maturation 6-8 weeks earlier, more broad shouldered fruit with a much less protruding stylar end and smooth fruit skin ('R5' has light vertical striations on the exterior of the fruit).

When compared to the male parent 'RY' (unpatented) which is a non-fruiting male pollinator; 'Y356' bears fruit When compared to the commercial variety 'W47' (U.S. Plant Pat. No. 22,777) which has the same male and female parents as 'Y356'; 'Y356' has significantly earlier fruit maturation.

When compared the commercial variety 'Y118' (U.S. Plant Pat. No. 20,956) which has the same male and female parents as 'Y356'; 'Y356' has a hairless fruit skin and an ovoid fruit shape.

I claim:

1. A new and distinct cultivar of kiwifruit plant as shown and described herein.

* * * * *